United States Patent
Theis et al.

(10) Patent No.: US 6,214,993 B1
(45) Date of Patent: Apr. 10, 2001

(54) PROCESS FOR PREPARING GUANINE UNDER SUPERATMOSPHERIC PRESSURE

(75) Inventors: Christoph Theis, Niederkassel; Stefan Bruhn, Handorf, both of (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/461,837

(22) Filed: Dec. 16, 1999

(30) Foreign Application Priority Data

Dec. 16, 1998 (DE) .............................. 198 57 949

(51) Int. Cl.⁷ ..................... C07D 473/18; A61P 31/12
(52) U.S. Cl. .............................................. 544/276
(58) Field of Search ................................. 544/276

(56) References Cited

U.S. PATENT DOCUMENTS

| | | | |
|---|---|---|---|
| 4,525,310 | 6/1985 | Theis et al. | 260/465.6 |
| 4,534,910 | 8/1985 | Peeters et al. | 260/465.6 |
| 4,701,526 | 10/1987 | Kobe et al. | 544/251 |
| 4,868,302 | 9/1989 | Schneider | 544/320 |
| 4,948,890 | 8/1990 | Schneider | 544/320 |
| 5,502,125 | 3/1996 | Bordeianu et al. | 526/140 |
| 5,663,338 | 9/1997 | Ramert et al. | 544/277 |
| 5,777,152 | 7/1998 | Theis et al. | 560/802 |

FOREIGN PATENT DOCUMENTS

| | | |
|---|---|---|
| 35 44 461 | 7/1986 | (DE) . |
| 37 23 874 | 1/1989 | (DE) . |
| 37 29 471 | 3/1989 | (DE) . |
| 41 36 114 | 5/1993 | (DE) . |
| 0 267 594 | 5/1988 | (EP) . |
| 0 304 004 | 2/1989 | (EP) . |
| 0 415 028 | 3/1991 | (EP) . |
| 0 541 003 | 5/1993 | (EP) . |

OTHER PUBLICATIONS

Roland K. Robins, et al., "Purines. II. The Synthesis of Certain Purines and the Cyclization of Several Substituted 4,5–diaminopyrimidines", J. Am. Chem. Soc., Vo. 75, pp. 263–266, Jan. 20, 1953.

*Primary Examiner*—Mukund J. Shah
*Assistant Examiner*—Thomas C McKenzie
(74) *Attorney, Agent, or Firm*—Oblon, Spivak, McClelland, Maier & Neustadt, P.C.

(57) ABSTRACT

A process for preparing guanine, in which 2,4-diamino-5-formylamino-6-hydroxypyrimidine (DAFHP) in formic acid is reacted at superatmospheric pressure, optionally in the absence of formamide and/or in the presence of catalytic amounts of an additive which acts as a reducing agent.

17 Claims, No Drawings

PROCESS FOR PREPARING GUANINE UNDER SUPERATMOSPHERIC PRESSURE

BACKGROUND OF THE INVENTION

1. Field of the Invention

The present invention relates to a process for preparing guanine (2-amino-1,9-dihydropurin-6-one) from 2,4-diamino-5-formylamino-6-hydroxypyrimidine (DAFHP) under pressure.

2. Description of the Background

The nucleic acid base guanine is of great importance as an intermediate for the synthesis of pharmacologically active compounds, in particular antiviral compounds. Guanine is required, for example, as a precursor for acyclovir which, according to DE 35 44 461, incorporated herein by reference, is suitable for treating viral infections.

The reaction of 4,5-diaminopyrimidine sulfates with formamide to give the corresponding purines is known from the literature (Robins et al., J. Am. Chem. Soc. 75 (1953) 263). Guanine is synthesized using 2,4,5-triamino-6-hydroxypyrimidine sulfate (TAHP sulfate).

According to DE 37 29 471, guanine can be obtained by heating a suspension of TAHP sulfate in formamide at up to 200° C. while distilling off the water of reaction formed.

A disadvantage is the partial decomposition of formamide at the high temperatures required, which results not only in formation of carbon monoxide and ammonia but also discolored crude guanine products which require costly purification. The need to use the TAHP, which is unstable in free form, in the form of its sulfate causes the formation of a large amount of inorganic salts, which represents a further disadvantage.

According to EP 0 415 028, guanine is obtained by reacting TAHP sulfate with alkali metal formate and formic acid. Although this process avoids the disadvantages associated with the use of formamide, it likewise leads to an economically and ecologically unfavorable formation of large amounts of unavoidable salts in the form of alkali metal sulfate in the reaction mixture.

The abovementioned processes based on TAHP sulfate proceed via the intermediate 2,4-diamino-5-formylamino-6-hydroxypyrimidine (hereinafter referred to as DAFHP) which is converted in situ into guanine.

According to DE 41 36 114, guanine can also be obtained starting from isolated DAFHP by heating in formamide to at least 140° C. The ratio of DAFHP to formamide is from 1:2–1:3. Up to 10% of formic acid can be added to the reaction mixture. The DAFHP used here is obtained, for example, by a process as described in EP 0 267 594, in which 2,4-diamino-6-hydroxy-5-nitrosopyrimidine is catalytically hydrogenated and converted into TAHP sulfate. After the hydrogenation, the reaction mixture is treated with formic acid, if desired with addition of a mineral acid, in order to obtain DAFHP in high yields. Although the process described in DE 41 36 114 is salt-free, it has the abovementioned disadvantages associated with the use of formamide (for example decomposition, costly purification of the end product). The guanine obtained as described in DE 41 36 114 has an assay purity (HPLC) of less than 98.0%. Losses in yield, therefore, occur as a result of purification.

According to German Application No. 198 39 013.0, guanine can also be prepared starting from isolated DAFHP by heating in boiling formic acid which may, if desired, be diluted by addition of small amounts of water. This process requires long reaction times of up to 20 hours.

All the above-mentioned processes have in common not only the process engineering disadvantages described but also the fact that they result in products which, even after being reprecipitated one or more times in the presence of activated carbon, sometimes contain considerable concentrations of a secondary component which fluoresces at 366 nm and can be detected by thin layer chromatography. Accordingly, there remains a need for a process for producing guanine which overcomes these disadvantages.

SUMMARY OF THE INVENTION

It is an object of the present invention to provide an industrial process for preparing guanine which does not have the disadvantages of the processes described above and which may provide guanine in a high space-time yield and in extremely high purity.

It is another object of the present invention to convert the guanine produced by the inventive to process to other compounds which may have pharmacological activities, e.g., antiviral agents.

The objects of the invention of the invention, and others, may be achieved with a process for preparing guanine starting from 2,4-diamino-5-formylamino-6-hydroxypyrimidine (DAFHP), in which isolated DAFHP in concentrated formic acid is subjected to a cyclocondensation under superatmospheric pressure at temperatures above the boiling point of the formic acid. The reaction may be conducted, optionally, in the presence of catalytic amounts of an additive(s) which acts as a reducing agent.

Accordingly, the objects of the invention may be accomplished with a process for preparing guanine, comprising reacting 2,4-diamino-5-formylamino-6-hydroxypyrimidine in formic acid at superatmospheric pressure.

A more complete appreciation of the invention and many of the attendant advantages thereof will be readily obtained as the same becomes better understood by reference to the following detailed description.

DETAILED DESCRIPTION OF THE PREFERRED EMBODIMENTS

The DAFHP starting material of the present process is preferably used in isolated form. The isolated DAFHP may be readily obtained, for example, by the process described in EP 0 267 594, incorporated herein by reference.

In the inventive method, it would not have been expected that a small temperature increase compared to the temperatures described in German application P 198 39 013.0, together with the use of pure formic acid under superatmospheric pressure would make possible virtually complete cyclocondensation of the DAFHP in surprisingly short reaction times, and that this would provide highly pure guanine after work-up.

It has also, very surprisingly, been found that addition of additives which act as reducing agents enable the purity of the resulting guanine to be significantly improved, particularly in respect of fluorescent secondary components, and that pure guanine virtually free of by-products may be obtained after work-up. In the process described herein, the additives which act as reducing agents may be alkali metal or alkaline earth metal salts of low-valence oxo-acids of sulfur. Particularly preferred agents are, for example, sodium sulfate or sodium dithionite. Based on DAFHP, up to 7.5 mol. % of the salts of the low-valence sulfur oxo acids may be employed.

Furthermore, noble metals having a reducing action may be used, preferably those of transition group VIII of the Periodic Table, which may, if desired, be applied in metallic form to a support. In this embodiment of the invention, particular preference is given to using metallic palladium or platinum, particularly in combination with carbon as support material.

Up to 10% by weight of the noble metals immobilized on supports, which have a moisture (water) content of up to 50% and, based on the dry mass of the catalyst, may contain up to 10% of noble metal, are used, based on DAFHP used.

Before use, the moist supported catalysts may be freed of residual, adhering water, for example by washing with concentrated formic acid, and then used while moist with formic acid, but, owing to the more complicated handling, this procedure provides no significant advantages. Rather, it has surprisingly been found that the supported noble metal catalysts used can be employed as commercial products, i.e. moist with water, where the noble metal content is preferably up to 5%, based on the dry mass of the supported catalyst.

Furthermore, it is also possible to use the supported noble metal catalyst isolated during the crude product purification a plurality of times for new DAFHP cyclocondensations without noticeable disadvantages, i.e. to recycle or to supplement it by addition of small amounts of fresh catalyst.

In the preferred embodiment, isolated DAFHP, additive which acts as reducing agent, and commercial concentrated formic acid are mixed and heated to temperatures of from 110–140° C. in a suitable pressure reactor. Reaction temperatures of from 120–130° C. are preferably employed and the reaction times are generally from 3–8 hours, preferably from 4–6 hours.

Shorter reaction times result in significant losses in yield resulting from unreacted DAFHP, while longer reaction times, although possible in principle, generally provide no significant improvements. Moreover, longer reaction times are contrary to the object of a high space-time yield in the process of the invention.

Low reaction temperatures prolong the reaction times as a consequence of sluggish DAFHP conversion, while higher reaction temperatures result in significantly higher decomposition rates of the formic acid used and thus economic disadvantages.

It has surprisingly been found that the process of the invention allows the use of higher DAFHP concentrations at very high space-time yields, which is a particular advantage of the present invention.

The molality of the reaction mixture (based on DAFHP) is, in the preferred embodiment, from 1.5–2.8, preferably 1.7–2.2. Under these conditions, the reaction mixtures employed are very readily stirrable.

The process of the present invention achieves a space-time yield of more than four times that obtained in, for example, EP 0 415 028. During the cyclocondensation, it is not necessary to limit the pressure which builds up as a result of the reaction temperature selected and the small degree of formic acid decomposition by means of suitable technical measures, although for practical reasons this can be done without disadvantage, e.g. in the pressure range 2–20 bar, preferably from 4–6 bar.

In the process of the invention, formic acid and water are distilled off, preferably under reduced pressure, after the reaction is complete. The water-containing formic acid recovered in this way is very pure and can be used in other processes. In particular, the recovered, water-containing formic acid can be used in the preparation of the DAFHP starting material, which represents a further advantage of the present process.

The crude guanine obtained may be purified in a known manner, the preferred embodiment allows, if desired, easy removal of support-containing noble metal catalysts.

In a particularly preferred embodiment for purifying the crude guanine, the latter is dissolved in aqueous alkali metal hydroxide, any supported noble metal catalyst present is filtered off and washed, and the solution or total filtrate obtained if filtration has been carried out is treated with activated carbon. Subsequently, guanine is usually isolated by precipitation, preferably by saponification precipitation, as described in DE-A-37 23 874, incorporated herein by reference. The process of the invention gives crude guanine in very good yields of, for example, 98% of theory. Thus, the yield of guanine in the present process may be at least 90%, preferably at least 95%, and most preferably, greater than 95%.

After purification, guanine can be obtained in good yields of usually 92% of theory or more as an extremely pure end product, with assays (HPLC) of more than 99.8% being achieved. Thus, the final yield of the purified guanine may be at least 92%, preferably at least 95%, more preferably at least 97%, and, most preferably, greater than 97%.

Analyses of these pure guanine by thin layer chromatography (TLC) show no detectable fluorescent secondary components compared to a guanine prepared as described in EP 0 415 028 and purified twice using 30% by weight each time of activated carbon (based on guanine used) together with saponification precipitations as described in DE 37 23 874, incorporated herein by reference.

The guanine prepared by the process according to the invention can be used as an intermediate for the synthesis of pharmacologically active compounds. In a particularly preferred embodiment, the pharmacologically active compound is an anti-viral agent. A preferred anti-viral agent is acyclovir. Acyclovir may be obtained from the guanine produced by the present process as described in, for example, DE 35 44 461, incorporated herein by reference.

Having generally described this invention, a further understanding can be obtained by reference to certain specific examples which are provided herein for purposes of illustration only and are not intended to be limiting unless otherwise specified.

EXAMPLES

Comparative Example 333.3 g of formic acid (98–100% strength) are placed in a glass autoclave fitted with a rotary stirrer and, while stirring, 101.4 g (0.6 mol) of DAFHP are introduced a little at a time (based on DAFHP, the molality is 1.8), the mixture is heated to 120° C. and the readily stirrable suspension is subsequently held at this temperature for 6 hours.

During the reaction, the pressure which builds up is maintained in the range from 4–5 bar by gradual release of pressure.

After cooling, the suspension is taken out and formic acid and water are almost completely distilled off in a waterpump vacuum.

The crude guanine obtained is purified in a known manner by dissolution in aqueous alkali metal hydroxide, treatment with activated carbon (30% by weight) and subsequent saponification precipitation.

The crude product obtained gives, after being purified once in this way, 84.0 g (92.6% of theory) of guanine having an assay (HPLC) of 99.8%. Quantitative TLC comparison with the doubly purified reference batch described prepared in accordance with EP-A-0 415 028 indicates the same concentrations of fluorescent secondary components.

Example 1

333.3 g of formic acid (98–100% strength) are placed in a glass autoclave and, while stirring, 101.4 g (0.6 mol) of DAFHP are introduced a little at a time (based on DAFHP, the molality is 1.8) and 4.0 g of Pd/C catalyst (50% moisture (water) content, Pd content: 5%) are added.

The mixture is heated to 120° C. in the glass autoclave and the readily stirrable suspension is held at this temperature for 5 hours, with the pressure which is established being maintained in the range from 4–5 bar by gradual release of pressure.

The reaction mixture taken out after cooling and venting is almost completely freed of formic acid and water by distillation in a water pump vacuum.

The crude guanine obtained in this way shows no residual DAFHP in the HPLC and is purified in a known manner by dissolution in alkali metal hydroxide, treatment with activated carbon (10% by weight) and subsequent saponification precipitation.

The crude product obtained gives, after being purified once by this method, 85.2 g (94.0% of theory) of guanine having an assay of 99.9% (according to HPLC).

Thin layer chromatography of this pure guanine shows no fluorescent secondary components.

Example 2

The procedure of Example 1 is repeated using 3.8 g of sodium sulfite (5.0 mol. %) and 5 hours at 123° C.

The reaction mixture obtained in this way is worked up as in Example 1 and the resulting crude guanine (residual DAFHP content according to HPLC: 0.3%) is purified as described in Example 1 using 30% by weight of activated carbon.

The pure guanine obtained in this way (84.4 g corresponding to 93.1% of theory) has an assay of 99.8% (HPLC) and displays only an extremely small amount of fluorescent secondary components in the quantitative TLC comparison with the doubly purified reference batch described.

Obviously, additional modifications and variations of the present invention are possible in light of the above teachings. It is, therefore, to be understood that within the scope of the appended claims, the invention may be practiced otherwise than as specifically described herein.

This application is based on German Patent Application No. 19857949.7, filed on Dec. 16, 1998, and incorporated herein by reference.

What is claimed as new and is intended to be secured by Letters Patent is:

1. A process for preparing guanine, comprising:

reacting 2,4-diamino-5-formylamino-6-hydroxypyrimidine in formic acid at superatmospheric pressure to produce guanine.

2. The process of claim 1, wherein isolated 2,4-diamino-5-formylamino-6-hydroxypyrimidine is reacted.

3. The process of claim 1, wherein said reacting is conducted at elevated temperature.

4. The process of claim 1, wherein said reacting is conducted in the presence of at least one additive which acts as a reducing agent.

5. The process of claim 4, wherein the additive is an alkali metal or alkaline earth metal salt of a low-valence oxo acid of sulfur.

6. The process of claim 4, wherein the additive is a noble metal of transition group VIII of the Periodic Table of the Elements, which is used in the form of the metal or is on a support material.

7. The process of claim 6, wherein the noble metal is palladium or platinum.

8. The process of claim 6, wherein noble metal is supported on carbon.

9. The process of claim 1, wherein the reaction is conducted at a temperature of from 110–140° C.

10. The process of claim 1, wherein the reaction is conducted at least at the pressure which is established when formic acid is heated to temperatures of from 110–140° C. under autogenous pressure.

11. The process of claim 1, wherein the reaction time is 3–8 hours.

12. The process of claim 1, wherein the reaction time is 4–6 hours.

13. The process of claim 1, wherein the molal concentration of 2,4-diamino-5-formylamino-6-hydroxypyrimidine in the reaction mixture is 1.5–2.8.

14. The process of claim 1, wherein the molal concentration of 2,4-diamino-5-formylamino-6-hydroxypyrimidine in the reaction mixture is 1.7–2.2.

15. The process of claim 1, wherein concentrated formic acid is used.

16. The process of claim 1, further comprising isolating the guanine.

17. The process of claim 1, further comprising distilling formic acid and water under reduced pressure after the reaction from the reaction medium, purifying the guanine in an aqueous alkaline solution using activated carbon, precipitating the guanine, and then isolating the guanine.

* * * * *